United States Patent
Vossgröne

(10) Patent No.: US 11,802,819 B2
(45) Date of Patent: Oct. 31, 2023

(54) METHOD OF SAMPLE PREPARATION ON A SPECTROMETRIC SAMPLE SUPPORT

(71) Applicant: Bruker Daltonik GmbH, Bremen (DE)

(72) Inventor: Alexander Vossgröne, Lilienthal (DE)

( * ) Notice: Subject to any disclaimer, the term of this patent is extended or adjusted under 35 U.S.C. 154(b) by 659 days.

(21) Appl. No.: 16/741,899

(22) Filed: Jan. 14, 2020

(65) Prior Publication Data

US 2020/0232889 A1    Jul. 23, 2020

(30) Foreign Application Priority Data

Jan. 21, 2019    (DE) .......................... 102019101389.5

(51) Int. Cl.
*G01N 1/28*    (2006.01)
*C12Q 1/18*    (2006.01)

(52) U.S. Cl.
CPC .................................... *G01N 1/28* (2013.01); *C12Q 1/18* (2013.01)

(58) Field of Classification Search
CPC .................................... G01N 1/28; C12Q 1/18
See application file for complete search history.

(56) References Cited

U.S. PATENT DOCUMENTS

| | | | |
|---|---|---|---|
| 5,397,316 A | 3/1995 | LaVon et al. | |
| 7,399,640 B2 | 7/2008 | Schürenberg et al. | |
| 9,638,636 B2 | 5/2017 | Tibbe et al. | |
| 10,011,860 B2 | 7/2018 | Lange et al. | |
| 2002/0051738 A1 | 5/2002 | Schürenberg | |
| 2012/0152041 A1 | 6/2012 | Maier | |
| 2012/0276575 A1* | 11/2012 | Fattinger | B01L 3/5025 435/307.1 |
| 2016/0298164 A1 | 10/2016 | Sparbier et al. | |
| 2018/0119086 A1 | 5/2018 | Markussen et al. | |
| 2018/0269050 A1 | 9/2018 | Schürenberg et al. | |

FOREIGN PATENT DOCUMENTS

| | | |
|---|---|---|
| CN | 1129395 A | 8/1996 |
| CN | 106053586 A | 10/2016 |
| DE | 10043042 A1 | 3/2002 |
| EP | 0804916 A1 | 11/1997 |
| EP | 1053784 A2 | 11/2000 |
| EP | 3376202 B1 | 8/2019 |
| JP | 2005134277 A | 5/2005 |
| JP | 2013515235 A | 5/2013 |
| JP | 2018029619 A | 3/2018 |
| JP | 2018155742 A | 10/2018 |
| KR | 1020180106950 A | 10/2018 |
| WO | 2018099500 A1 | 6/2018 |

OTHER PUBLICATIONS

Ghebremedhin, B., Halstenbach, A., Smiljanic, M., Kaase, M., & Ahmad-Nejad, P. (2016). MALDI-TOF MS based carbapenemase detection from culture isolates and from positive blood culture vials. Annals of clinical microbiology and antimicrobials, 15(1), 1-6 (Year: 2016).*
Idelevich, E. A., Sparbier, K., Kostrzewa, M., & Becker, K. (2017). Rapid detection of antibiotic resistance by MALDI-TOF mass spectrometry using a novel direct-on-target microdroplet growth assay. Clinical Microbiology and Infection, 24(7), 738-743. (Year: 2017).*
Rygiewicz, P. T., Miller, S. L., & Durall, D. M. (1988). A root-mycocosm for growing ectomycorrhizal hyphae apart from host roots while maintaining symbiotic integrity. Plant and Soil, 109(2), 281-284 (Year: 1988).*
Idelevich, E.A. et al., "Direct blood culturing on solid medium outperforms an automated continuously monitored broth-based blood culture system in terms of time to identification and susceptibility testing", New Microbes and New Infections, 10:19-24, Mar. 2016.
Gobom, Johan, et al., "α-Cyano-4-hydroxycinnamic Acid Affinity Sample Preparation. A Protocol for MALDI-MS Peptide Analysis in Proteomics" Anal. Chem. 2001, 73, 434-438.

* cited by examiner

*Primary Examiner* — Robert J Yamasaki
*Assistant Examiner* — Trevor Kane
(74) *Attorney, Agent, or Firm* — BENOIT & COTE, INC.

(57) ABSTRACT

The invention relates to a method for sample preparation on a spectrometric sample support, comprising the steps of: (i) providing the sample support with an arrangement of individual liquid droplets, for example of washing liquid or nutrient solution, each of which has microorganism sediments enclosed in it; (ii) locating a plate of an absorbent material containing cotton fibers, for example, above the sample support; (iii) lowering the plate vertically onto the sample support in such a way that microorganism sediments and plate come into contact, whereby the droplets of liquid are absorbed into the absorbent material; (iv) lifting the plate, which is locally enriched with droplet liquid, off the sample support, thereby exposing the microorganism sediments that are depleted of liquid; and (v) preparing the exposed microorganism sediments for spectrometric measurement, by means of infrared spectrometry or MALDI time-of-flight mass spectrometry, for example.

11 Claims, 4 Drawing Sheets

METHOD OF SAMPLE PREPARATION ON A SPECTROMETRIC SAMPLE SUPPORT

BACKGROUND OF THE INVENTION

Field of the Invention

The invention relates to a method of sample preparation on a spectrometric sample support, where the sample support contains an arrangement of individual droplets of liquid, each of which has microorganism sediments enclosed in it.

Description of the Related Art

The prior art is explained hereinafter with reference to a special aspect. This shall not be understood as a limitation, however. Useful further developments and modifications of what is known from the prior art can also be used above and beyond the comparatively narrow scope of this introduction, and will easily be evident to experts skilled in the art in this field after reading the following disclosure.

Earlier experiments have shown that microorganisms that are suspended in a droplet of nutrient solution accumulate as a sediment of microorganisms on a flat substrate after a relatively short standing time (or "rest time") of up to one hour. The microorganisms that are sedimented there in a kind of "biofilm" can be carefully separated from residual liquid and remaining suspended particles by bringing an absorbent cloth into contact with the droplets, for example. After this "dehydration", the species of microorganisms can be reliably determined with a subsequent mass spectrometric measurement, cf. international application WO 2018/099500 A1. This finding was astonishing because, contrary to expectation, it was found that the cell sediment of the microorganisms of interest is not removed together with the liquid as it is being drawn off. This finding allows the cultivation (or incubation) of microorganisms for the purpose of promoting growth and also the preparation for an analytical measurement on one and the same substrate, such as a sample support plate for insertion into the ion source of a mass spectrometer or a specimen slide for insertion into the measuring slot of an infrared spectrometer.

A fully developed scientific explanation for this microbial behavior in a droplet on a flat substrate is not yet available, but it is assumed that physical interactions between the surface of the sample support and the cells of the microorganisms, and also adhesion processes resulting from the biochemical and biophysical properties of the cell surface of the microorganism, are responsible for the preferred adhesion or sedimentation on the substrate.

In a further development of the art known from WO 2018/099500 A1, the application EP 3 376 202 A1 proposes a mask with indentations or holes, whose inner surfaces are brought into contact with the peripheral areas of the droplets and remove the droplet liquid laterally via capillary forces. The center of the droplets, underneath which most of the microorganism sediment is located, is not to be touched in this process, since it was feared that direct contact with the sediment would necessarily lead to depletion of the microorganisms ("plating effect"), and thus to the associated sensitivity losses in the subsequent analytical measurement.

The localized, non-contact removal of liquid, either by means of the profiled mask or by placing a rigid plate onto a vertical spacer that surrounds the droplets, as described in EP 3 376 202 A1, has the disadvantage that enough residual liquid of the droplets can still remain on the sediment on the substrate to cause interference with the subsequent analysis of the microorganism sediment and further purification measures may become necessary.

There is therefore a need to separate the individual microorganism sediments from the covering droplets of liquid sufficiently completely, while ensuring that as little of the material of the microorganism sediments as possible is removed together with the liquid in this separation process. Further objectives to be achieved by the invention are immediately clear to the person skilled in the art from reading the disclosure below.

SUMMARY OF THE INVENTION

The invention relates to a method of sample preparation on a spectrometric sample support, comprising the following steps: (i) Provide the sample support, which contains an arrangement of individual droplets of liquid, each of which has microorganism sediments enclosed in it, (ii) Provide a plate made of an absorbent material, (iii) Lower the plate vertically onto the sample support in such a way that microorganism sediments and plate come into contact, whereby the droplets of liquid are absorbed into the absorbent material, (iv) Lift the plate, which is locally enriched with droplet liquid, off the sample support, thereby exposing the microorganism sediments that are depleted of liquid, and, where necessary, after any residual film of liquid which may remain on the cell sediments of the microorganisms has been allowed to dry, and (v) Prepare the exposed microorganism sediments for spectrometric measurement, for example a subsequent infrared or mass spectrometric measurement.

In different embodiments, the plate can contain a swelling absorbent material and can be lowered until there is only a small gap between it and the sample support so that a supernatant of the droplets comes into contact with the plate and is absorbed by it, whereby the absorbent material undergoes localized swelling at the sites where the droplet liquid has been absorbed, and thus makes contact with the microorganism sediments. A plate made of blotting board whose material has a suitable swelling characteristic has been found to be particularly suitable for this version. Blotting board is particularly known from the restoration and archiving of moisture-sensitive works of art and is essentially a neutral, acid-free, absorbent and low-lint fleece board with a high proportion of cotton fibers, which can amount to more than 50%, in particular 60%.

The choice of gap size that initially does not allow contact can be tested very simply by lowering a plate coated with an easily rubbed-off color onto the sample support. If traces of color are found on the sample support after the plate has been lifted off again, the gap was not large enough to prevent direct contact and must be readjusted. It is thus easy to experimentally set gaps of fractions of a millimeter, which can be closed through the swelling reaction of an absorbent material such as blotting board when localized liquid absorption occurs until contact is made with the microorganism sediment.

In various alternative embodiments, the plate can be placed directly onto the sample support and gently pressed down so that the arrangement and the plate make all-over contact.

The invention is based on the unexpected and therefore surprising finding that it is possible to lower a flat and low-lint plate made of an absorbent material down to a flat sample support and bring it into contact, or even to place the plate partly onto the sample support and press it down slightly in such a way that capillary forces draw almost all the liquid supernatant of a droplet into the absorbent material without the microorganism sediment hidden below being depleted to such an extent that a subsequent spectrometric analysis of the sample support would not provide informative results because there was too little biomaterial. Although a film of liquid does remain after the plate is lifted off (vertically), this is so thin that it dries within seconds.

It is preferable for the sample support and/or plate to be spring-mounted with relative respect to each other so that excessive pressure applied when the plate is pressed down is taken up by the springs. The elastic deformation of the springs ensures that a constant contact pressure is exerted by the plate on the sample support. The pressure can be adapted to the requirements by setting a suitable spring constant and adjusted so that the microorganism sediment is not adversely affected by the application of pressure.

In various embodiments, a plate surface facing toward the sample support can be moistened slightly before being lowered, for example with deionized water or methanol/ethanol, in order to accelerate the absorption of the liquid from the droplet. The slight moistening and surface wetting of the fibers located at the periphery of the plate particularly facilitate the formation of a liquid contact or liquid bridge between the droplets deposited on the sample support and the fiber matrix of the plate so that the fiber fabric at the periphery is surface-wetted right from the outset and does not have to first undergo time-consuming wetting or soaking when the plate comes into liquid contact with the droplets on the sample support.

It is preferable for the plate to have absorbent fibers made of cellulose and/or plant fibers, in particular cotton, nitrocellulose, nylon, glass fiber, polyvinylidene difluoride or combinations thereof. Blotting board as a particularly suitable material can contain a mixture of 60% cotton fibers and 40% bleached (pH neutral and acid-free) cellulose, for example.

Conventional volumes of droplets can correspond to around one to twelve microliters. These volumes in the form of uniform droplets roughly correspond to a diameter of two or three millimeters across the surface of the sample support.

In infrared spectrometric or mass spectrometric analysis, in particular, for example MALDI time-of-flight analysis, 48, 96, 384 or 1536 individual droplets can be arranged in a predefined (and regular) pattern on the sample support. Of course, it is also possible to mark the sample support with preferred spots for the droplets, for example lyophilic circular areas in a lyophobic environment. The diameter of the droplets will then adjust itself in line with the dimension of the lyophilic circular area, as occurs with standardized anchor plates of the AnchorChip™ type.

The droplets can in particular mainly contain liquid, which is used in sample preparation methods and sample processing methods for infrared spectrometry or mass spectrometry. The droplets can contain nutrient solution, for example, and the sedimented material can contain microorganisms, which have been cultivated in these droplets of nutrient solution and then deposited. Separation of the nutrient solution from sedimented microorganisms can particularly serve as a preparatory step of a sample for infrared spectrometric or mass spectrometric identification (e.g., by means of IR transmission spectroscopy or MALDI time-of-flight mass spectrometry) according to species/subspecies, or a different characterization of the microorganisms such as the rapid determination of resistance/sensitivity of the microorganisms against antimicrobial substances such as antibiotics and antimycotics.

Where necessary, an antimicrobial substance can be added to the nutrient solution, for example to determine the minimum inhibitory concentration of microorganisms by means of incubation in the nutrient solution droplet enriched with antibiotics or antimycotics.

Additionally or alternatively the droplets can contain a washing liquid used for a sample preparation method (for example an aqueous solution or pure deionized water) or other liquid working media. For example, the washing liquid of sample spots that have been coated with pre-dried microorganism sediment, or with dried matrix substance and microorganism sediment, can be absorbed with the plate. The washing liquid is preferably chosen such that the matrix substance or the matrix crystal lattice with embedded sample crystals is not dissolved, e.g., with an α-cyano-4-hydroxycinnamic acid affinity preparation for in-situ desalination (see Gobom et al., Anal. Chem. 73, 2001, 434-438).

In various embodiments, it is possible to use a metal, glass or ceramic plate as the spectrometric sample support. Possible embodiments are in particular polished stainless-steel plates or adaptations thereof, such as the so-called anchor plates (such as AnchorChip™, Bruker Daltonik GmbH), which are plates which contain alternating lyophilic and lyophobic surfaces isolated from each other on a stainless-steel substrate. A glass plate as an infrared spectrometric specimen slide for transmission measurement is also possible. The sample support can be reusable or disposable.

A conventional, standardized sample support for ionization by matrix-assisted laser desorption (MALDI) can contain a regular arrangement of 48, 96, 384 or 1536 sample spots. The dimensions of a sample support and a plate of absorbent material can each be 127.76 mm (length)×85.48 mm (width), corresponding to a microtiter plate, with a thickness of around two to five millimeters, as long as they are congruent. The sample spot arrangement and thus the arrangement of the droplets on the sample support covers a smaller area than the sample support itself, however.

There can also be provision for a frame for the plate or a guide for the sample support, into which the plate is inserted, which assists with the guidance and alignment of the plate while it is being lowered onto the arrangement of droplets, as is described in EP 3 376 202 A1, which together with all its contents is to be included here by reference. The frame can, for example, be permanently connected to the plate, in particular by folding over a projecting, cut-to-size border of the absorbent material and then impregnating it with a polymer, which then sets. The frame can also be injection-molded onto the outer perimeter of the plate using a suitable polymer.

The plate is preferably fabricated from a stiff and low-lint fabric. Plant fibers and/or cellulose are ideal for this. It can, for example, have fibrous materials such as cotton fiber, nitrocellulose, nylon, glass fiber, polyvinylidene difluoride, or combinations thereof, for example blotting board containing around 60% cotton fibers and 40% bleached (pH neutral and acid-free) cellulose. Rigid materials are particularly suitable for automated methods of absorbing liquid. The rigid plates can easily be removed from a store by specially adapted handling devices such as robot arms, before being clamped into an adapted holder, transferred to the liquid absorption step and then set down at the required location, and disposed of also, where necessary.

Regarding the production of the plate, it is possible to provide a continuous length of the absorbent material and then cut off plate pieces according to the desired outer contour. For use in a microbiology laboratory, it is expedient to select the external dimensions of the plate such that the liquid absorbed, together with any suspended microorganisms that it may still contain, cannot penetrate to the edge or the top surface of the plate, so that the plate can be gripped there and moved without any danger of contamination after it has undergone localized enrichment with liquid.

BRIEF DESCRIPTION OF THE DRAWINGS

The invention can be better understood by referring to the following illustrations. The elements in the illustrations are not necessarily shown to scale, but are primarily intended to illustrate the principles of the invention (largely schematically). In the illustrations, the same reference numbers designate corresponding elements in the different views.

DETAILED DESCRIPTION

While the invention has been illustrated and explained with reference to a number of embodiments, those skilled in the art will recognize that various changes in form and detail may be made to it without departing from the scope of the technical teaching as defined in the attached patent claims.

Figure 1A:
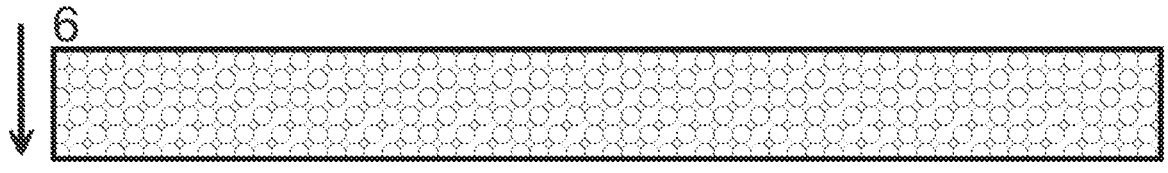
FIGS. 1A to 1E show schematic representations of an example embodiment for a method whereby a plate of absorbent material is placed onto a droplet-bearing sample support.
Figure 1B:
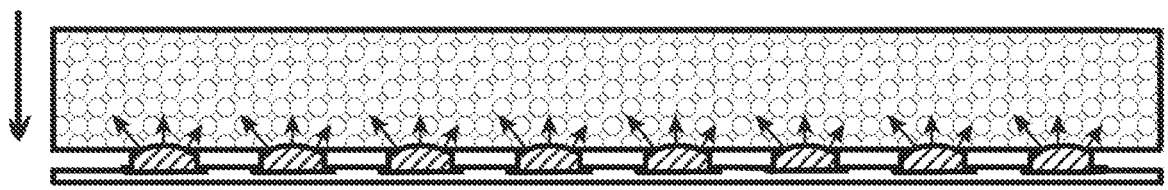
Figure 1C:
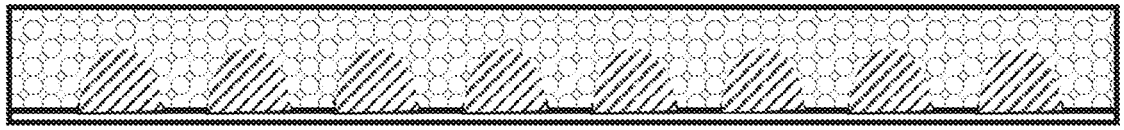

FIG. 1A depicts an arrangement of droplets (2) along a row of eight on a sample support (4), which can correspond to a MALDI sample support plate or a specimen slide plate suitable for infrared spectrometry. A plate (6) of absorbent material is positioned above the sample support (4). The plate (6) is moved slowly in the vertical direction toward the sample support (4), whereby the droplets (2) come into contact with the absorbent material of the plate (6) as from a certain lowering point onward so that the droplet liquid is absorbed by the plate material (6) by means of capillary forces, FIG. 1B. In contrast to earlier disclosures, this lowering movement can end with the plate (6) being brought to rest on the sample support (4) as shown, FIG. 1C. All-over contact can thus be produced between plate (6) and droplet arrangement (2), which leaves behind less residual liquid from the droplets (2) on the microorganism sediments, and thus facilitates the subsequent spectrometric measurements of the sediments.

Surprisingly, it was found that a previously assumed "plating effect" is significantly less pronounced than was feared. What the term "plating effect" refers to is that many cells of the microorganisms are removed from the sediment by being transferred onto the plate when they come into direct contact with the absorbent material of the plate (6), thus making a subsequent measurement more difficult because the amount of biomaterial available is reduced, which is why non-contact removal of the liquid was favored in earlier disclosures. Experiments carried out in-house by the applicant, in which the plates used to absorb the liquid were incubated, show that colonies of microorganisms can form on the plate surface at those sites where droplet liquid has been absorbed. Nevertheless, the quantity of biomaterial that was "removed by the plating" was so small, contrary to expectation, that the subsequent spectrometric analyses of the material remaining on the sample support (4) was not adversely affected.

It has not yet been possible to find a fully developed scientific explanation for these advantageous characteristics, but it is assumed that the interaction between the fibers of the plate material and the microorganisms is very small so that neither adheres well to the other, which counteracts the plating effect. It is furthermore assumed that limiting the plate movement to a purely vertical lowering onto the sample support while avoiding lateral shearing movements, unlike the earlier disclosure where lateral movements were indeed recommended, also reduces and possibly eliminates the risk of smearing the microorganism biofilm, which could lead to a transfer of cells from the sample support to the plate material.

Figure 1D:
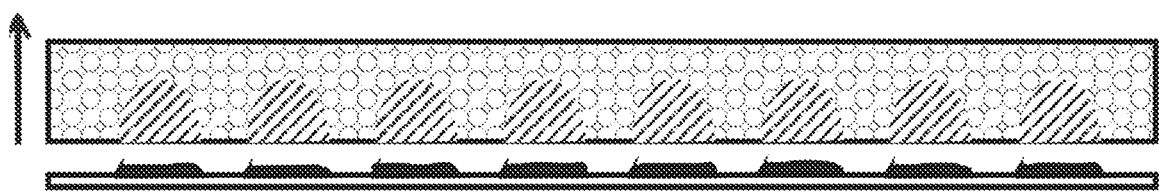

After making contact, the droplet liquid is absorbed in a very short time, usually fractions of a second, where necessary helped by slightly pre-moistening the plate material. Afterwards, the plate (6), which is locally enriched with liquid, can be lifted off again and removed, FIG. 1D. The liquid absorbed is securely retained in the capillary matrix of the plate (6), so there is no danger that it will drip out again while the plate is being lifted off vertically and thereby contaminate the sample support (4). On the contrary, it is a very safe and reliable way to remove the liquid. The partially soaked plate (6) is typically disposed of as consumable material, which is advantageous for microbiological applications. Where appropriate, it could also be washable and then reusable, however.

Figure 1E:

As has already been explained above, the microorganism sediments enclosed in the droplets (2) are not removed by the gentle absorption of the liquid by means of capillary forces, but remain largely centrally on the surface of the sample support (4) where the droplets (2) were deposited. The sedimented material, from which the liquid has now been removed, is thus available for further processing, such as sample preparation for infrared spectrometry, ionization by matrix-assisted laser desorption or similar processing steps, indicated by the pipetting of a working medium, for example matrix substance for MALDI, at (8) in FIG. 1E.

The distance between the plate edge and the nearest droplet preferably corresponds to at least the droplet radius on the surface of the sample support. It is safer with the droplet diameter, in order to avoid biohazardous constituents being drawn too close to the edge when the liquid is absorbed into the absorbent material, as the edge of the plate may be gripped by the laboratory staff. A similar safe distance should be observed for the minimum thickness of the plate in order to prevent the absorbed liquid penetrating through to the plate surface facing away from the absorption of the liquid.

In a modification of the method explained above, the plate (16), after being lowered toward and making contact with the sample support (14), can also be lightly pressed against the sample support to ensure there is all-over contact between plate (16) and arrangement (12) or sample support surface, which allows the most complete absorption of liquid. To prevent excessive pressure being exerted, particularly when it is pressed down by hand (for example by inexperienced laboratory staff), which could have a detrimental effect on the microorganism sediment, plate (16) and sample support (14) can be spring-mounted with relative respect to each other, as is schematically indicated by the coiled springs (18) in FIGS. 2A to 2D. It shall be understood that the sample support (14), the plate (16) or both elements can be spring-mounted to achieve the desired effect, although only the springs of the sample support (14) are illustrated in the sequence shown.

Figure 2A:
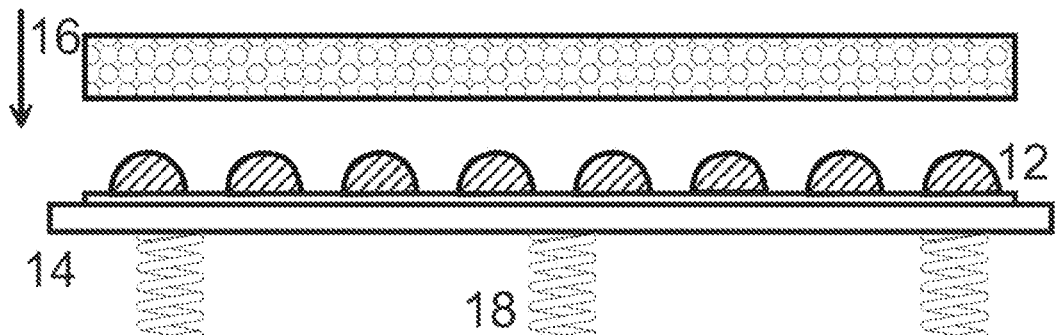
FIGS. 2A to 2D schematically illustrate a modification of the method, whereby springs take up excess pressure applied when the plate is pressed onto the sample support, and thus ensure the pressure is applied uniformly.
Figure 2B:
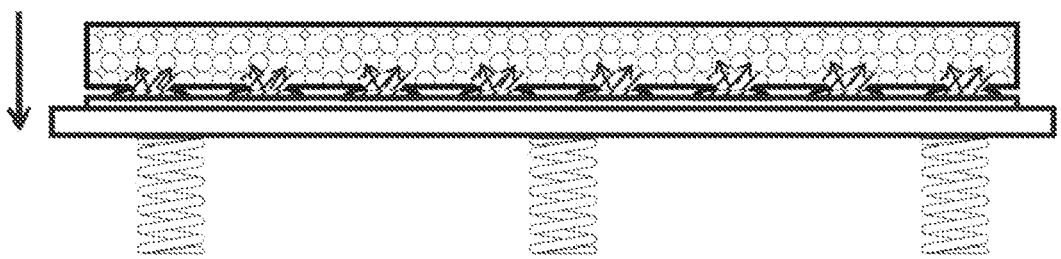
Figure 2C:
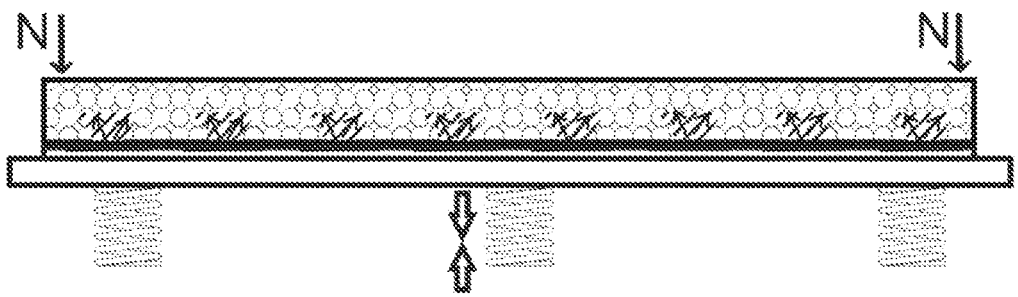
Figure 2D:
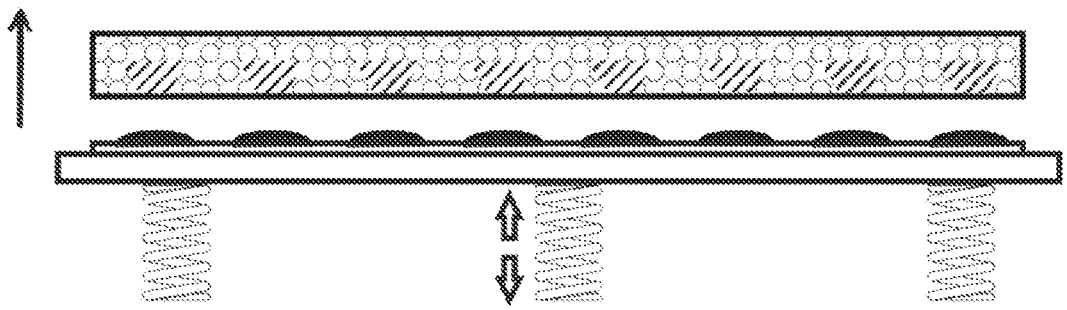

A plate (16) made of an absorbent material is lowered toward the sample support (14), which bears the droplets of liquid (12) (FIG. 2A). In this state, the springs (18) are not compressed. As soon as the plate (16) makes contact with the droplet supernatant, which takes place even before contact is made with the sample support surface, the liquid of the droplet is absorbed into the absorbent material of the plate (16) (FIG. 2B). In this state, too, the springs (18) are still not compressed. As soon as the plate (16) touches the sample support (14), resistance to the lowering movement becomes noticeable. Pressure can now be exerted to ensure a uniform and, in particular, all-over contact between plate (16) and sample support surface or arrangement (12) and to absorb residual liquid as much as possible (FIG. 2C). The springs (18) are now compressed as a function of the applied pressure N and the spring constant, and thus prevent excessive pressure being exerted on the microorganism sediments. After a timespan of fractions of a second, when the liquid has been absorbed into the plate material, the plate (16) can be lifted off vertically again, and thus exposes the microorganism sediments, which are now depleted of liquid and are accessible for further processing on the sample support (14) (FIG. 2D). The springs (18) then relax again in this process.

It shall be understood that the coiled springs (18) from the aforementioned example serve only to illustrate the cushioning principle. In the methods presented here, other cushioning mechanisms can be used also, as a specialist in the field deems expedient.

Figure 3:
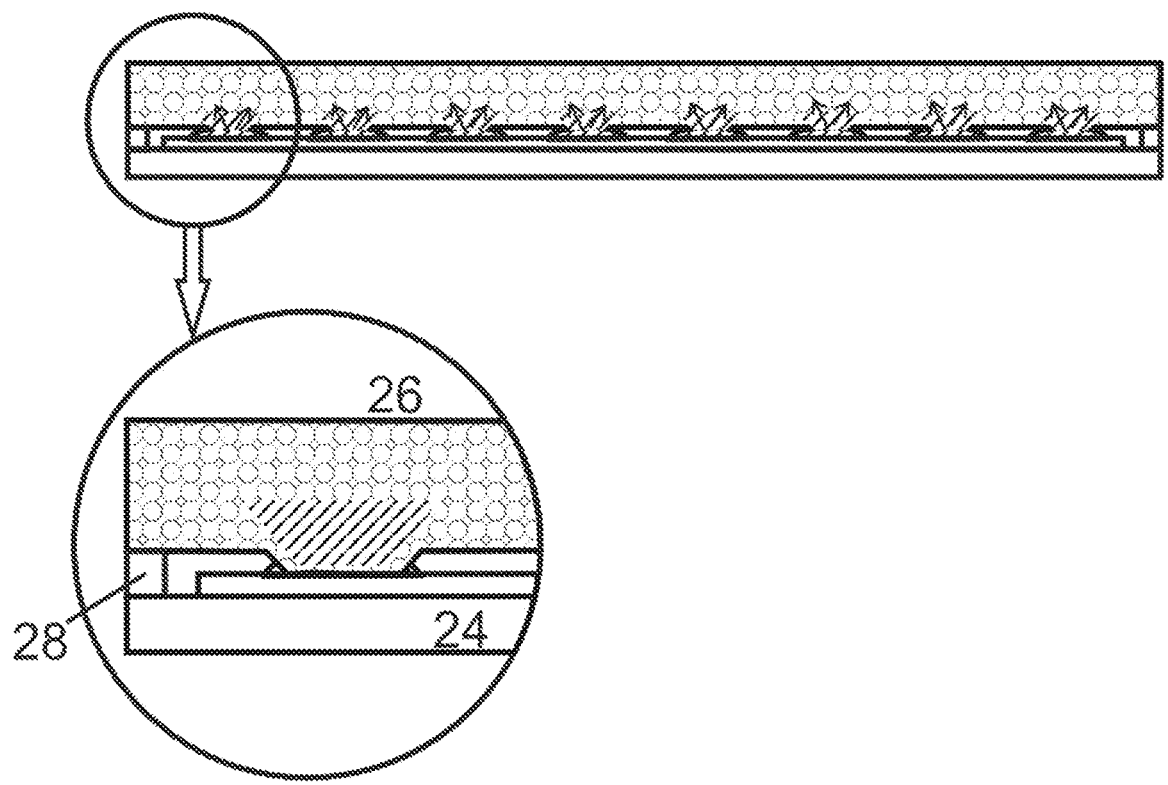
FIG. 3 is a schematic representation of an example embodiment for a method whereby a plate made of material that swells is lowered toward the sample support until there is only a small gap between plate and sample support.

Embodiments have been described above in which the absorbent plate (26) is brought into direct contact with the sample support (24). However, it is also possible to maintain a slight gap between the plate (26) and the sample support (24), for example by placing the plate on a lateral rim (28) when it is fabricated from a swelling, absorbent material (FIG. 3). When the plate surface makes contact with the droplet supernatants, there is localized absorption of the liquid into the plate (26), which leads to an increase in volume ("swelling") there so that the swollen material makes gentle contact with the microorganism sediments (as shown in the enlarged section in FIG. 3). It has been found that the sediment is not adversely affected by this gentle contact. In particular, only a few microorganism cells are transferred onto the plate surface ("plating effect"), but the liquid of the droplet is absorbed more completely than is possible with the techniques published previously, which operated strictly with a gap because of the use of non-swelling materials. The quantity of residual liquid that remains on the sample support (24) after the plate (26) with localized saturation is lifted off (vertically) is thus reduced, facilitating the subsequent spectrometric measurements.

In order to simplify the handling of the plate, it can be inserted or clamped into a frame. The frame can, for example, be dimensioned such that it fits flush around a sample support on which an array of droplets is located, as described in EP 3 376 202 A1. It can be designed either as a disposable item, which is disposed of together with the saturated plate, or as a washable and reusable item. Possible embodiments include a frame with stepped inner contour, on which the plate can be placed so as to be friction locked. If the frame slides down around the outer contour of the sample support, contact with the liquid is established as from a specific point. The frame furthermore has the advantage that it ensures there is reliable alignment and guidance of the plate relative to the array of droplets.

In an alternative embodiment, likewise described in principle in EP 3 376 202 A1, the frame can be fixed firmly to the plate. A projecting, cut-to-size border of the absorbent material can be folded over, for example, and then impregnated with a polymer, which then sets to ensure stability and rigidity (single-piece variant). Where necessary, the frame can also be injection molded onto the plate at the outer perimeter using a suitable polymer.

Likewise known from EP 3 376 202 A1 is the technique whereby a sample support that bears the array of droplets is inserted into a guide which encloses it on all sides. The plate can then have similar dimensions to the sample support and slowly slide from the top guide opening downward onto the sample support. Grip recesses in the guide walls can make it easier to insert the sample support and plate and to lift them out again.

Figure 4:
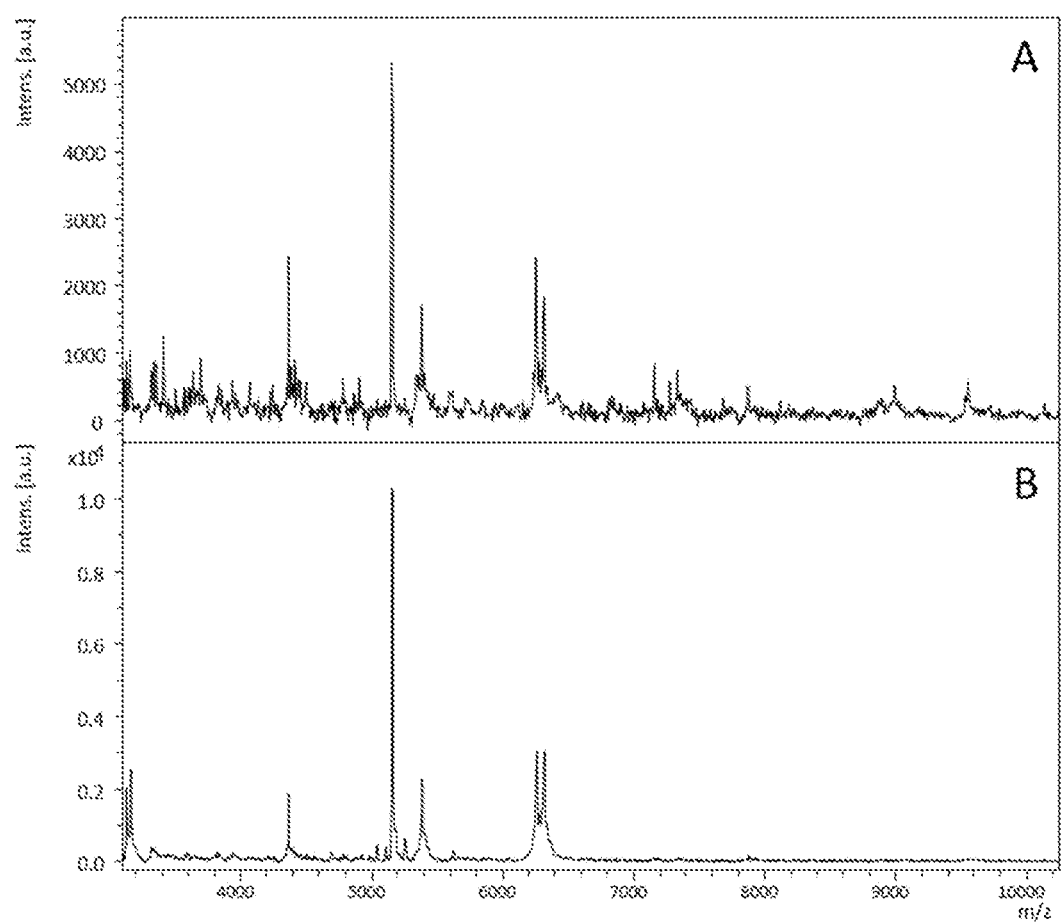
FIG. 4 depicts spectra obtained by MALDI time-of-flight mass spectrometry after the removal of culture supernatants from an enterobacterial sediment, once using a non-contact method, top diagram A, as is known for example from E. A. Idelevich et al., Clin. Microbiol. Infect. 2018 (7): 738-743, where Whatman® cellulose filter paper was used as the absorbent material, and once using a contacting method in accordance with the principles of the invention, bottom diagram B; vertical axis: intensity in arbitrary units; horizontal axis: mass-to-charge ratio m/z.

FIG. 4 is a comparison of two mass spectra that depicts measurement data, which illustrate the advantages of the method described here. The (almost) complete removal of a droplet supernatant, here culture or nutrient solution supernatant after bacteria incubation, directly on a MALDI sample support, in accordance with the principles of this disclosure (bottom portion B of figure) and thus also the removal of contaminations, e.g., constituents of the nutrient medium or salts, which can interfere with the subsequent measurement, leads to better quality measurement data in the form of higher ion signal intensities and an improved signal-to-noise ratio.

Regarding a determination of the antibiotic susceptibility (cephalosporin antibiotic: ceftazidime) of Gram-negative bacteria analyzed, the contacting method according to the invention and the non-contact method according to the prior art produced consistent results after 4 h/4.5 h/5 h incubation at 95%/100%/100% and 93%/93%/92%, respectively, compared to a conventional nutrient solution micro-dilution method (20 h incubation), which emphasizes the great benefit of these procedures.

Further embodiments of the invention are conceivable in addition to the embodiments described by way of example. With knowledge of this disclosure, those skilled in the art can easily design further advantageous sample preparation methods for an infrared spectrometric or mass-spectrometric measurement using a desorbing ionization method, which are to be covered by the scope of protection of the patent claims, including any equivalents.

The invention claimed is:

1. A method for sample preparation on a spectrometric sample support, comprising the steps of:
    providing an arrangement of individual droplets of liquid on the sample support, each of which has microorganism sediments enclosed in it;
    locating a plate of absorbent material above the sample support;
    lowering the plate vertically onto the sample support in such a way that the microorganism sediments and plate come into contact, whereby the droplets of liquid are absorbed into the absorbent material;

lifting the plate off the sample support, thereby exposing the microorganism sediments that are depleted of liquid; and preparing the exposed microorganism sediments for spectrometric measurement.

2. The method according to claim 1, wherein the plate contains a swelling absorbent material and is lowered until there is a small enough gap between it and the sample support that a supernatant of the droplets comes into contact with the plate and is absorbed by it, whereby the absorbent material undergoes localized swelling at the sites where the droplet liquid is absorbed and makes contact with the microorganism sediments.

3. The method according to claim 1, wherein the plate is placed directly onto the sample support and pressed against it so that the entire arrangement of droplets makes contact with the plate.

4. The method according to claim 3, wherein the sample support and/or the plate are spring-mounted with relative respect to each other so that pressure applied is taken up by springs when the plate is pressed down.

5. The method according to claim 1, further comprising moistening a plate surface facing the sample support before said step of lowering.

6. The method according to claim 1, wherein the plate comprises absorbent fibers of cellulose and/or plant fibers.

7. The method according to claim 1, wherein a volume of one of said droplets is approximately one to twelve microliters.

8. The method according to claim 1, wherein the liquid droplets comprise nutrient solution or washing liquid.

9. The method according to claim 8, wherein the liquid droplets further comprise an antimicrobial substance.

10. The method according to claim 1, further comprising performing an infrared or mass spectrometric measurement after preparing the exposed microorganism sediments.

11. The method according to claim 1, wherein any remaining residual liquid film on the microorganism cell sediments is allowed to dry after lifting the plate before preparing the exposed microorganism sediments.

* * * * *